US010415367B2

(12) United States Patent
Galford

(10) Patent No.: US 10,415,367 B2
(45) Date of Patent: Sep. 17, 2019

(54) SYSTEM AND METHODS FOR ESTIMATION OF INTRA-KEROGEN POROSITY OF DOWNHOLE FORMATION SAMPLES FROM PYROLYSIS TESTS AND BASIN MODELING DATA

(71) Applicant: Halliburton Energy Services, Inc., Houston, TX (US)

(72) Inventor: James E. Galford, Missouri City, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 489 days.

(21) Appl. No.: 14/654,892

(22) PCT Filed: Dec. 27, 2012

(86) PCT No.: PCT/US2012/071794
§ 371 (c)(1),
(2) Date: Jun. 23, 2015

(87) PCT Pub. No.: WO2014/105021
PCT Pub. Date: Jul. 3, 2014

(65) Prior Publication Data
US 2015/0330203 A1  Nov. 19, 2015

(51) Int. Cl.
*G01V 1/40* (2006.01)
*G01V 3/18* (2006.01)
(Continued)

(52) U.S. Cl.
CPC .......... *E21B 44/005* (2013.01); *E21B 47/065* (2013.01); *E21B 49/00* (2013.01);
(Continued)

(58) Field of Classification Search
CPC ........ E21B 49/00; E21B 47/06; E21B 47/065; E21B 44/005; G01N 33/241; G05B 17/00; G06F 17/10
See application file for complete search history.

(56) References Cited

U.S. PATENT DOCUMENTS 4,629,702 A   12/1986  Fan
7,117,092 B2* 10/2006  Jacobson ............... G01V 5/101
                                                         702/8
(Continued)

OTHER PUBLICATIONS

International Preliminary Report on Patentability issued in related PCT Application No. PCT/US2012/071794, dated Jul. 9, 2015 (10 pages).
(Continued)

*Primary Examiner* — Toan K Le
(74) *Attorney, Agent, or Firm* — Alan Bryson; Baker Botts L.L.P.

(57) ABSTRACT

Systems and methods for determining kerogen porosity of a formation for downhole operations are described herein. An example method may include obtaining core pyrolysis data from a wellbore disposed in a formation. A thermal characteristic of the formation proximate to the wellbore, such as a time-temperature burial history of the formation, may also be determined. A kerogen porosity of the formation may be calculated based, at least in part, on the pyrolysis data and the thermal characteristic, and a downhole operation may be performed based, at least in part, on the calculated kerogen porosity.

15 Claims, 4 Drawing Sheets

(51) Int. Cl.
*G01V 5/04* (2006.01)
*G01V 9/00* (2006.01)
*E21B 44/00* (2006.01)
*G05B 17/00* (2006.01)
*G06F 17/10* (2006.01)
*E21B 47/06* (2012.01)
*E21B 49/00* (2006.01)
*G01N 33/24* (2006.01)

(52) U.S. Cl.
CPC ........... *G01N 33/241* (2013.01); *G05B 17/00* (2013.01); *G06F 17/10* (2013.01)

(56) References Cited

U.S. PATENT DOCUMENTS

| | | | |
|---|---|---|---|
| 7,500,517 B2 | 3/2009 | Looney et al. | |
| 7,613,665 B2* | 11/2009 | Chen | G06N 3/086 706/16 |
| 8,050,866 B2* | 11/2011 | Jacobson | G01V 5/101 702/8 |
| 8,692,185 B2* | 4/2014 | Guo | G01V 5/101 250/269.4 |
| 2009/0145598 A1* | 6/2009 | Symington | E21B 43/24 166/250.01 |
| 2010/0155078 A1 | 6/2010 | Walters et al. | |
| 2010/0212904 A1 | 8/2010 | Billman | |
| 2010/0270015 A1 | 10/2010 | Vinegar et al. | |
| 2013/0113479 A1* | 5/2013 | Chen | E21B 49/08 324/303 |
| 2013/0200890 A1* | 8/2013 | Hursan | G01V 3/32 324/303 |
| 2015/0234090 A1* | 8/2015 | Galford | G01V 1/48 166/250.01 |

OTHER PUBLICATIONS

Modica, et al., "Estimation of kerogen porosity in source rocks as a function of thermal transformation: Example from the Mowry Shale in the Powder River Basin in Wyoming," AAPG Bulletin (Jan. 2012), pp. 87-108.

Waples, et al., "The universality of the relationship between vitrinite reflectance and transformation ratio," Organic Geochemistry (1988), pp. 383-388.

Sweeney et al., "Evaluation of a simple method of vitrinite reflectance based on chemical kinetics," AAPG Bulletin (Oct. 2012), pp. 1559-1570.

Burnham, "A simple kinetic model of petroleum formation and cracking," Lawrence Livermore National Laboratory Report UCID-21665.

Waples, et al., "The art of maturity modeling. Part 2: alternative models and sensitivity analysis," AAPG Bulletin (Jan. 1992).

Dahl, et al., "A new approach to interpreting Rock-Eval S2 and TOC data for kerogen quality assessment," Organic Geochemistry (2004).

Tissot, et al., "Thermal history of sedimentary basins, maturation indices, and kinetics of oil and gas generation," AAPG Bulletin (Dec. 1987).

Ritter, et al., "Adsorption of petroleum compounds in vitrinite: implications for petroleum expulsion from coal", International Journal of Coal Geology, vol. 62 (2005), pp. 183-191.

Loucks, et al., "Morphology, genesis, and distribution of nanometer-scale pores in siliceous mudstones of the Mississippian Barnett Shale", Journal of Sedimentary Research, vol. 79 (2009), pp. 848-861.

Quirein, et al., "Review and comparison of three different gas shale interpretation approaches", SPWLA 53rd Annual Logging Symposium, Jun. 16-20, 2012, 16 pages.

International Search Report and Written Opinion issued in related PCT Application No. PCT/US2012/071794, dated Nov. 4, 2013, 14 pages.

Official Action issued in related Canadian application No. 2,891,081 dated Mar. 21, 2018 (6 pages).

Luca, "Rock properties distribution" In: "integrated reservoir studies: Chapter 4—Rock Properties", Institut Fracais du Petrole, pp. 144-146, Dec. 31, 2001 (Dec. 31, 2001).

Official Action issued in related Canadian application No. 2,891,081 dated Mar. 26, 2019 (4 pages).

Bordenave (ed). "Applied Petroleum Geochemistry" 1993 Editions Technip, Paris. ISBN 2-7108-0629-0; published Apr. 1993. pp. 405-407.

* cited by examiner

SYSTEM AND METHODS FOR ESTIMATION OF INTRA-KEROGEN POROSITY OF DOWNHOLE FORMATION SAMPLES FROM PYROLYSIS TESTS AND BASIN MODELING DATA

CROSS-REFERENCE TO RELATED APPLICATION

The present application is a U.S. National Stage Application of International Application No. PCT/US2012/071794 filed Dec. 27, 2012, which is incorporated herein by reference in its entirety for all purposes.

BACKGROUND

The present disclosure relates generally to well drilling and hydrocarbon recovery operations and, more particularly, to systems and methods for estimation of intra-kerogen porosity from core pyrolysis and basin modeling data.

Existing well drilling operations require information on formation characteristics to aid in drilling decisions and wellbore placement. Recently, kerogen porosity has become a characteristic of interest, due in part to the increasing interest in source rock reservoirs. Kerogen comprises organic compounds that make up portions of sedimentary rocks, which through thermal maturation expel hydrocarbons. Kerogen porosity may refer generally to the hydrocarbon storage capacity of the formation. Typical methods for direct measurement of a formation's kerogen porosity include the use of scanning transmission electron microscopy (STEM) and scanning electron microscopy (SEM). Unfortunately, these techniques are time-consuming and expensive, and are typically not scalable to an entire formation or basin.

FIGURES

Some specific exemplary embodiments of the disclosure may be understood by referring, in part, to the following description and the accompanying drawings.

Figure 1:
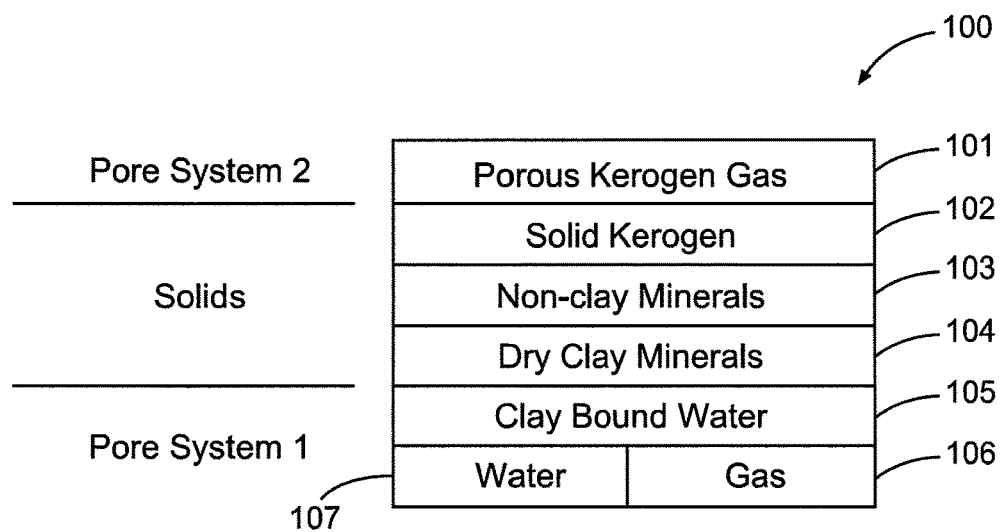
FIG. 1 illustrates an example dual porosity model, according to aspects of the present disclosure.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure relates generally to well drilling and hydrocarbon recovery operations and, more particularly, to systems and methods for estimation of intra-kerogen porosity from core pyrolysis and basin modeling data.

Illustrative embodiments of the present disclosure are described in detail herein. In the interest of clarity, not all features of an actual implementation may be described in this specification. It will of course be appreciated that in the development of any such actual embodiment, numerous implementation-specific decisions must be made to achieve the specific implementation goals, which will vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the disclosure. Embodiments of the present disclosure may be applicable to horizontal, vertical, deviated, multilateral, u-tube connection, intersection, bypass (drill around a mid-depth stuck fish and back into the well below), or otherwise nonlinear wellbores in any type of subterranean formation. Certain embodiments may be applicable, for example, to logging data acquired with wireline, slickline, and LWD. Embodiments described below with respect to one implementation are not intended to be limiting.

According to embodiments of the present disclosure, systems and methods for determining kerogen porosity of a formation for downhole operations are described herein. An example method may include obtaining pyrolysis data from a wellbore disposed in a formation. The pyrolysis data may be obtained from a core sample of the formation. A thermal characteristic of the formation proximate to the wellbore may also be determined. In certain embodiments, the thermal characteristic of the formation may comprise a time-temperature burial history, as will be described below, or another thermal maturity measurement. The thermal characteristic may be determined, for example, using logging measurements from the borehole, a pre-existing formation model based on the formation type, some combination of the two, or another method that would be appreciated by one of ordinary skill in view of this disclosure. A kerogen porosity of the formation may be calculated based, at least in part, on the pyrolysis data and the thermal characteristic, and a downhole operation may be performed based, at least in part, on the calculated kerogen porosity. Notably, by utilizing pyrolysis data and thermal characteristics of the formation, rather than STEM and SEM measurements of formation samples, the process of determining kerogen porosity may be faster and less expensive. Additionally, by avoiding the STEM and SEM measurements, which are taken on small samples, the kerogen porosity value can be extrapolated and extended to an entire formation, instead of the area immediately surrounding a single borehole.

At least one stratum in a source rock formation may comprise kerogen, which is characterized by a mixture of organic chemical compounds that make up a portion of the organic matter in the stratum. When heat is applied to kerogen, the kerogen may be naturally converted to hydrocarbons, such as oil and gas. The process of conversion may create pores within the kerogen, trapping some of the hydrocarbons. The kerogen porosity of an example stratum, and the source rock formation generally, may correspond, therefore, to the ratio of the volume of all the pores in kerogen to the volume of the whole kerogen, and may identify the possible hydrocarbon storage capacity or the formation and correlate to the amount of recoverable hydrocarbons. FIG. 1 shows an example dual porosity model 100 for a source rock reservoir, where the formation is composed of porous kerogen and porous minerals. Other dual porosity models are possible, depending on the formation, as would be appreciated by one of ordinary skill in view of this disclosure. Such models may be generated using various wireline or logging measurements described above, as would be appreciated by one of ordinary skill in the art in view of this disclosure. Each of the portions shown in the dual porosity model 100 may correspond to generic representations of elements of a source rock formation. In other words, the various gasses, fluids, and minerals identified may be dispersed throughout the source rock and are only illustrated as defined portions for ease of modeling.

According to certain embodiments of the present disclosure, porous kerogen may comprise a non-solid volume, $\varphi_{pk}$, filled with in-situ generated hydrocarbons, such as oil or gas, consistent with the natural conversion process. The porous kerogen may also comprise a solid volume, $1-\varphi_{pk}$, representing the otherwise unconverted portion of the kerogen. The non-solid volume of the porous kerogen, $\varphi_{pk}$, may further correspond to kerogen porosity of the formation, as represented by the volume of porous kerogen gas 101 in the dual porosity model 100. Although a gas-filled kerogen is shown in dual porosity model 100, an oil-filled kerogen may also be modeled with a similar model.

The dual porosity model 100 may comprise a first pore system that includes clay bound water 105, porous mineral water 107, and porous mineral gas 106. The water and mineral gas within the first pore system may represent typical byproducts of hydrocarbon production, but byproducts which must be accounted for in formation modeling. Above the first pore system is a solid portion that may include non-clay minerals 103, dry clay minerals 104, and solid kerogen 102. As will be appreciated by one of ordinary skill in the art, the non-clay minerals 103, dry clay mineral 104, and solid kerogen 102 may be found interspersed throughout strata of the formation, without definite boundaries. Finally, the dual porosity model 100 includes the porous kerogen gas 101.

In certain embodiments, values for the kerogen porosity $\varphi_{pk}$ of the formation, as well as some of the other values in the dual porosity model 100 may be calculated using an information handling system, which may receive hundreds of data points from logging measurements, survey measurements, pyrolysis data, etc. For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. The processing resources may include other processors such a graphical processing units (GPU). Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

Figure 2:
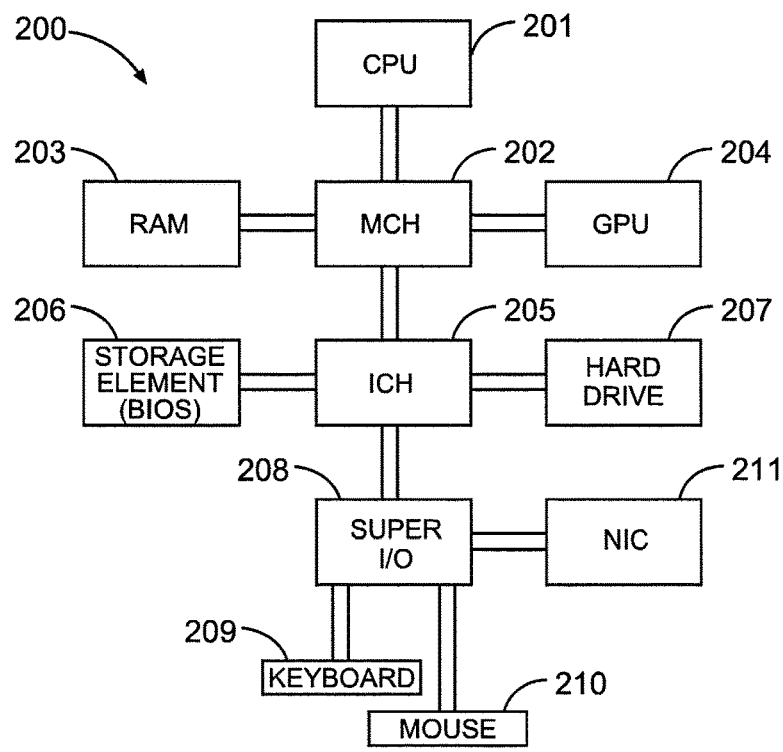
FIG. 2 illustrates an example information handling system, according to aspects of the present disclosure.

Shown in FIG. 2 is a block diagram of an example information handling system 200. A processor or CPU 201 of the information handling system 200 may be communicatively coupled to a memory controller hub or north bridge 202. The memory controller hub 202 may be coupled to RAM 203 and a graphics processing unit 204. Memory controller hub 202 may also be coupled to an I/O controller hub or south bridge 205. I/O hub 205 may be coupled to storage elements of the computer system, including a storage element 206, which may comprise a flash ROM that includes the BIOS of the computer system. I/O hub 205 is also coupled to the hard drive 207 of the computer system. The hard drive 207 may be characterized as a tangible computer readable medium that contains a set of instructions that, when executed by the processor 201, causes the information handling system 200 to perform a pre-determined set of operations. For example, according to certain embodiments of the present disclosure, and as will be discussed below, the hard drive 207 may contain instructions that when executed cause the CPU 201 to perform complex computations on certain data sets that will be described below.

In certain embodiments, I/O hub 205 may also be coupled to a super I/O chip 208, which is itself coupled to several of the I/O ports of the computer system, including keyboard 209, mouse 210, and one or more parallel ports. The super I/O chip 208 may further be coupled to a network interface card (NIC) 211. The information handling system 200 may receive measurements or logs various over the NIC 211, for processing or storage on a local storage device, such as hard drive 207. In certain embodiments, the data may be stored in a dedicated mass storage device (not shown). The information handling system may then retrieve data from the dedicated storage device, and perform computations on the data using algorithms stored locally within hard drive 207.

Figure 3:
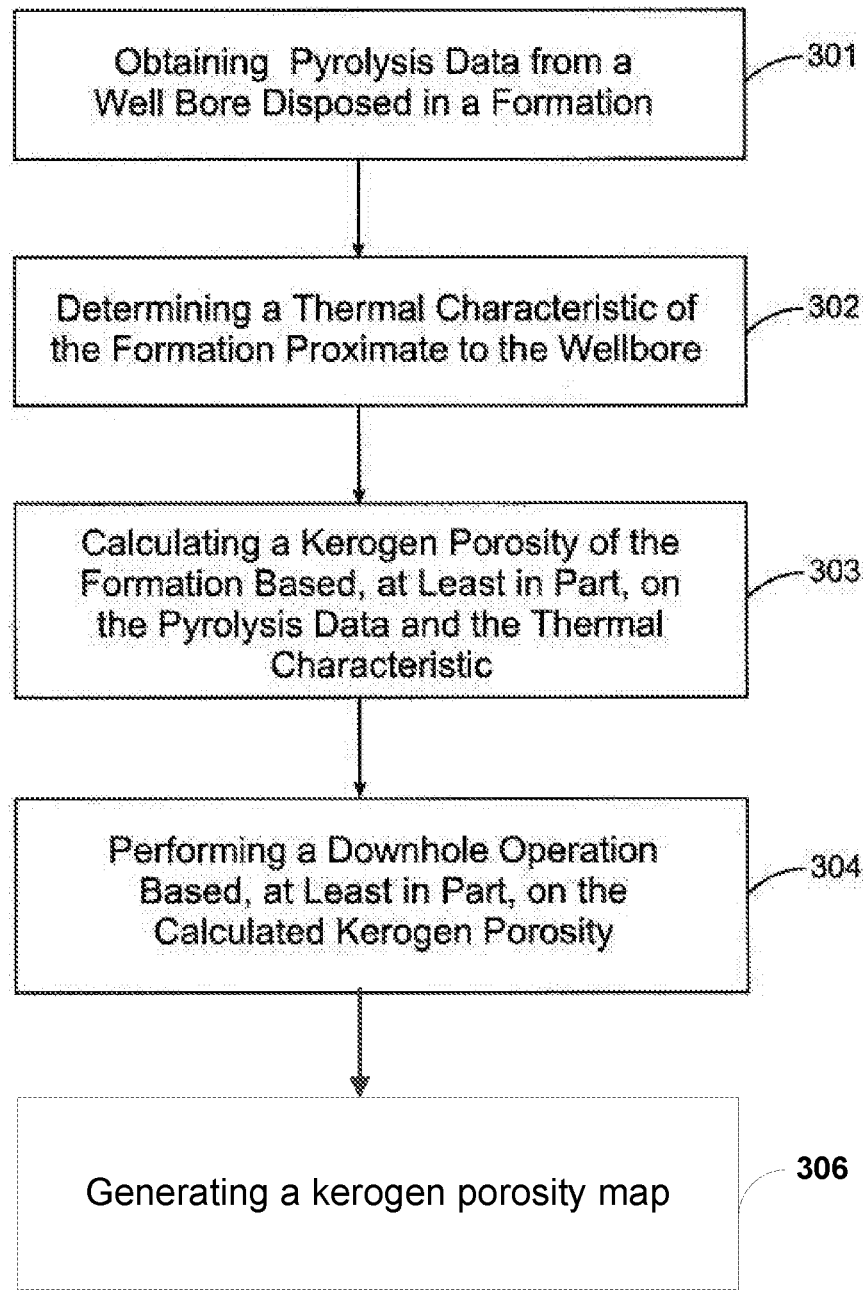
FIG. 3 illustrates an example method, according to aspects of the present disclosure.

FIG. 3 illustrates an example method for determining kerogen porosity of a formation for downhole operations, according to aspects of the present disclosure, some of which may be implemented in an information handling system, as will be described below. Step 301 comprises obtaining pyrolysis data from a wellbore disposed in a formation. In certain embodiments, obtaining pyrolysis data from a wellbore disposed in a formation may comprise taking core samples from the formation and subjecting the core samples to pyrolysis testing either on-site at the wellbore location, or at an offsite location. Pyrolysis refers to the thermochemical decomposition of organic material at elevated temperatures without the participation of oxygen. Pyrolysis data may be generated during pyrolysis testing and may characterize the chemical composition of the core as well as certain temperature responses of the core. This pyrolysis data may be included in a data set that is stored at an information handling system and used to calculate a kerogen porosity $\varphi_{pk}$, as will be described below.

Figure 4:
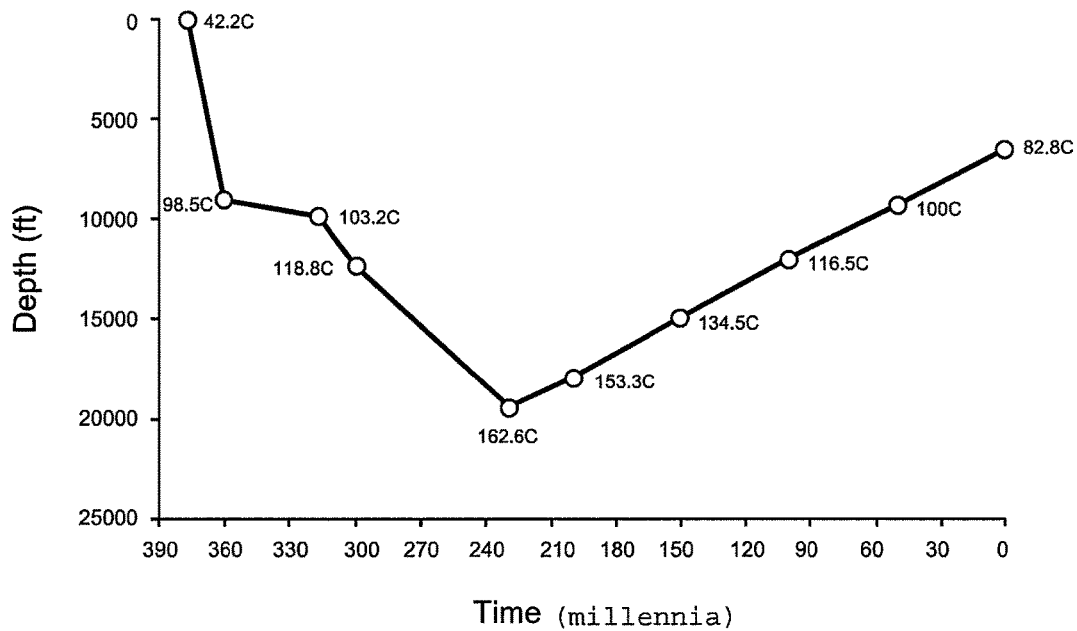
FIG. 4 illustrates an example time-temperature burial history, according to aspects of the present disclosure.

Step 302 comprises determining a thermal characteristic of the formation proximate to the wellbore. In certain embodiments, the thermal characteristic may comprise a time-temperature burial history of the formation, although other thermal characteristics or thermal maturity measurements of the formation may be used. FIG. 4 illustrates an example time-temperature burial history. As can be seen, a time-temperature burial history may characterize the temperate to which a formation or a segment of a formation was subjected at a particular depth and geological time (in millennia). As will be appreciated by one of ordinary skill in view of this disclosure, the time-temperature burial history may be determined through a variety of techniques including seismic survey, downhole logging, etc. Like the pyrolysis data, the time-temperature burial history may be included in a data set that is stored at an information handling system and used to calculate a kerogen porosity $\varphi_{pk}$, as will be described below Step 303 comprises calculating a kerogen porosity of the formation based, at least in part, on the pyrolysis data and the thermal characteristic. The kerogen porosity $\varphi_{pk}$ may be calculated, for example, in an information handling system according to complex instructions and algorithms stored therein. In certain embodiments, calculating the kerogen porosity of the formation based, at least in part, on the pyrolysis data and the thermal characteristic may comprise solving equation (1).

$$\varphi_{pk}=TOC_i*C_c*k*TR*p_b/p_k \qquad \text{Equation (1)}$$

In equation (1), $\varphi_{pk}$ may comprise the non-solid volume of porous kerogen in the formation, $TOC_i$ may comprise the initial organic carbon weight fraction of the formation; $C_c$ may comprise the fraction of carbon in the formation that is convertible to hydrocarbon; k may comprise a scale factor representing the kerogen mass equivalent to a convertible carbon mass (typically k equals approximately 0.95/0.85); TR may comprise the transformation ratio of the kerogen; $p_b$ may comprise the formation density; and $p_k$ may comprise the kerogen density.

In certain embodiments, solving equation (1) may comprise calculating $TOC_i$, TR, $C_c$ using at least one of the pyrolysis data and the time-temperature burial history. The other values in equation (1) may be known or calculated from other sources, including survey or log data that would be appreciated by one of ordinary skill in the art in view of this disclosure. In certain embodiments, calculating the transformation ratio TR may comprise applying a kinetic model of kerogen cracking to the time-temperature burial history. The data from a time-temperature burial history similar to that in FIG. 4 can be input into a system of concurrent first-order Arrhenius reaction equations to simulate the progression of kerogen cracking reactions. Equation (2) illustrates an example Arrhenius equation that can be used to predict the reaction rate of kerogen, k, as a function of the reaction activation energy $E_a$, the universal gas constant R, frequency factor A, and absolute temperature, T.

$$k=A*e^{\hat{}}(-E_a/(R*T)) \qquad \text{Equation (2)}$$

In certain embodiments, the distribution of activation energies may be pre-determined and correspond to a particular kerogen type. For example, the distribution of activation energies used in the equations may the distributions identified by researchers at Lawrence Livermore National Laboratory, as would be appreciated by one of ordinary skill in view of this disclosure.

According to certain embodiments of the present disclosure, the conversion of organic matter over time into hydrocarbons may be represented by equation (3), where k is the reaction rate from equation (2), V is the amount of organic matter, and t is time.

$$dV/dt=-k*V \qquad \text{Equation (3)}$$

Moreover, because kerogen conversion is a complex process and is it assumed that a set of parallel reactions with different activation energies can be used, a time-dependent reaction for the $i^{th}$ reaction component can be found using equations (4) and (5).

$$dV_i/dt=-V_i*A*e^{\hat{}}(-E_i/(R*T)) \qquad \text{Equation (4)}$$

$$dV/dt=\Sigma(i)\ dV_i/dt \qquad \text{Equation (5)}$$

Additionally, the amount of unconverted organic matter from the $i^{th}$ reaction maybe given by equation (6), with $V_{oi}$ being the initial amount of the ith reaction component.

$$V_i=V_{oi}-\int(dV_i/dt)dt \qquad \text{Equation (6)}$$

Finally, the transformation ratio TR may be calculated using equation (7), with $f_i$ representing a stoichiometric factor corresponding to the overall fraction of the $i^{th}$ reaction in the conversion process, and $V_0$ representing the total amount of the organic matter.

$$TR=1-V/V_0=1-\Sigma(i)f_i*V_i/V_{0i} \qquad \text{Equation (7)}$$

Figure 5:
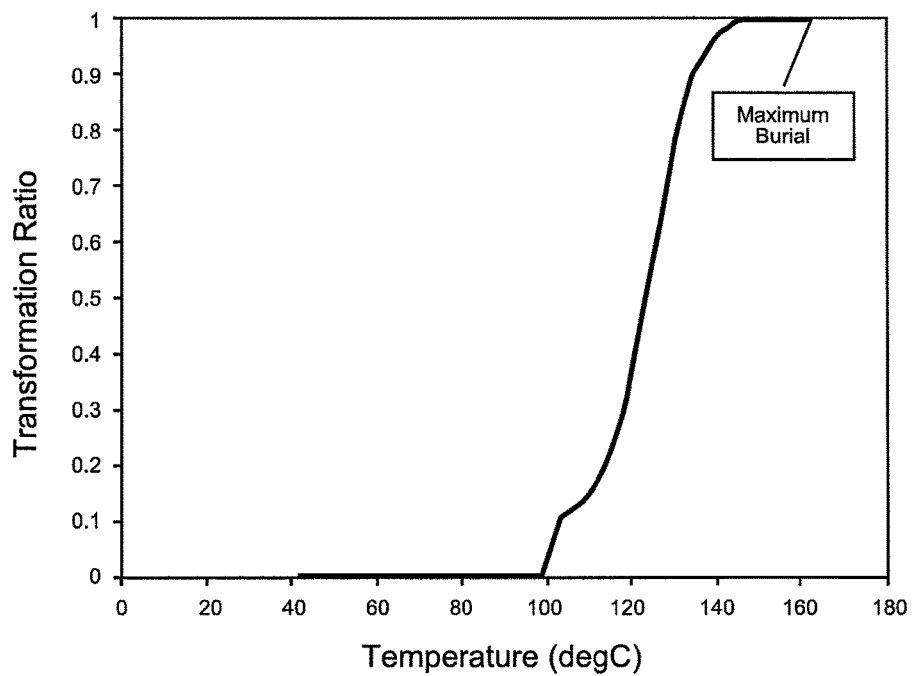
FIG. 5 illustrates an example output of a kinetic model, according to aspects of the present disclosure.

FIG. 5 illustrates an example transformation ratio to temperature plot generated using the above kinetics and the time-temperature burial history illustrated in FIG. 4. In certain embodiments, the method may further comprise correlating the output of the kinetic model, as seen in FIG. 5, with at least one vitrinite reflectance for the formation. The vitrinite reflectance may comprise a measurement of the maturity of organic matter with respect to whether it has generated hydrocarbons or could be an effective source rock. In certain embodiments, the vitrinite reflectance may be determined through direct measurements of the formation. In certain other embodiments, the vitrinite reflectance may be determined by applying a kinetics model to the time-temperature burial history of the formation. This may be useful when there are not enough samples to accurately determine vitrinite reflectance directly.

Figure 6:
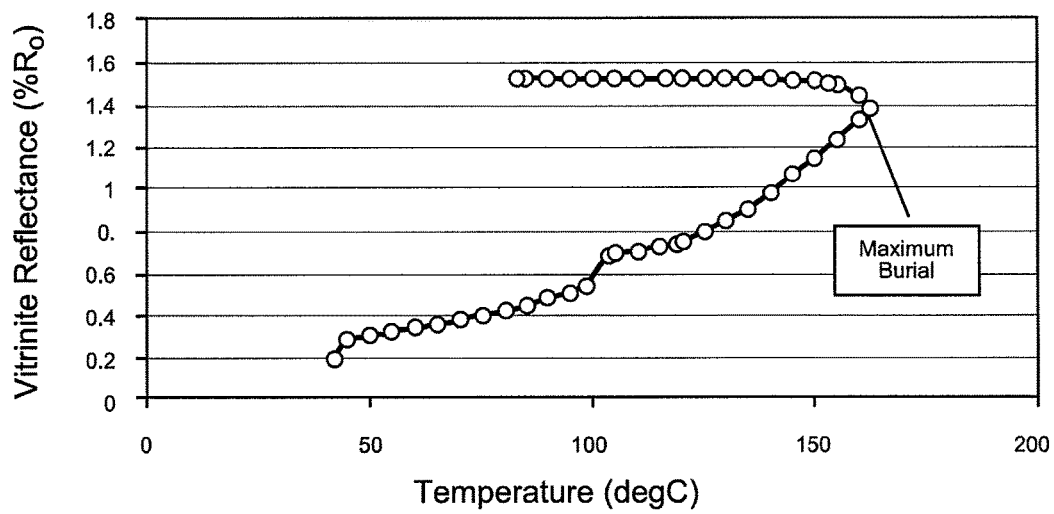
FIG. 6 illustrates an example vitrinite reflectance plot, according to aspects of the present disclosure.
Figure 7:
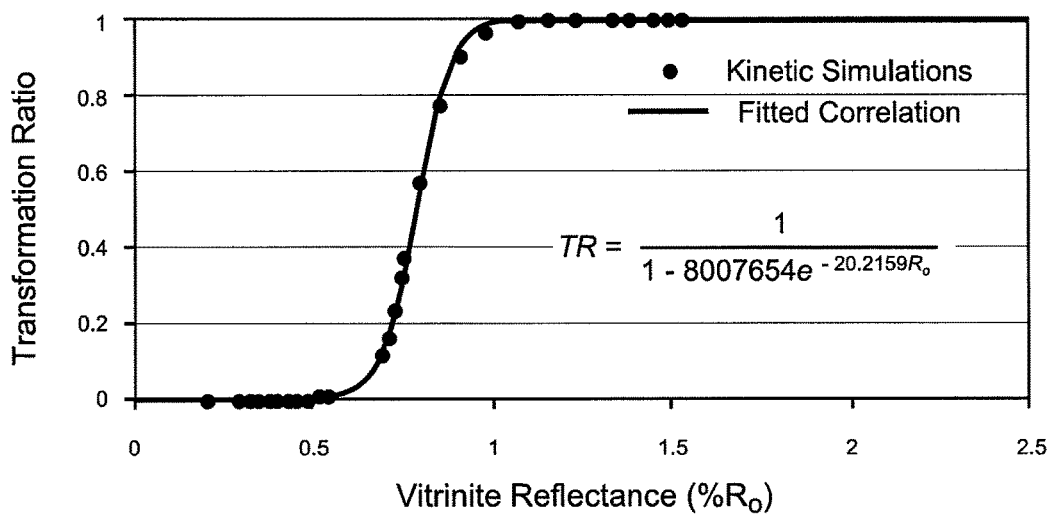
FIG. 7 illustrates an example transformation ratio/vitrinite reflectance correlation, according to aspects of the present disclosure.

FIG. 6, for example, illustrates an example vitrinite reflectance plot generated using a kinetics model. Correlating the output of the kinetic model, as seen in FIG. 5, with at least one vitrinite reflectance for the formation may comprise, for example, combining the results shown in FIGS. 5 and 6 as shown in FIG. 7. As can be seen in FIG. 7 the combined data may fit a correlation function between the transformation ratio and the vitrinite reflectance for a given source reservoir. This may improve the calculated value of the transformation value and therefore the calculated value of the kerogen porosity.

Additionally, according to certain embodiments, calculating the initial organic carbon weight fraction of the formation, $TOC_i$, in equation (1), may comprise solving equation (8), where $S_2$ comprises the remaining hydrocarbon potential of a pyrolysis sample, $\alpha$ comprises the average carbon weight fraction in the hydrocarbons formed during conversion of kerogen, and TOC comprises the organic carbon weight fraction of the sample.

$$TOC_i=TOC+((S_2*TR*\alpha)/(1-TR)) \qquad \text{Equation (8)}$$

Notably, $\alpha$ may be expressed in terms of the elemental composition of the produced hydrocarbons according to equation (9), in which C and H are the atomic weights of carbon and hydrogen and g is the number of hydrogen atoms in the produced hydrocarbons.

$$\alpha=(0.001*C)/(C+(g*H)) \qquad \text{Equation (9)}$$

In certain embodiments, calculating the fraction of carbon in the formation that is convertible to hydrocarbon, $C_c$, in equation (1), may comprise solving equation (10), where $S_{2i}$ comprises the original hydrocarbon generation potential of the formation.

$$C_c=0.085*(S_{2i}/TOC_i) \qquad \text{Equation (10)}$$

Notably, the fraction of carbon that can be converted into hydrocarbons, also known as labile carbon, may be linked to an original kerogen hydrogen index, $HI_i$, because the carbon conversion can only proceed as long as convertible hydrogen is available. Experimental data suggests that this fraction can be estimated using equation (10).

Referring again to FIG. 3, step 304 may comprise performing a downhole operation based, at least in part, on the calculated kerogen porosity. Performing the downhole operation based at least in part on the determined kerogen porosity may include using the calculated kerogen porosity within a dual porosity model to calculate additional formation characteristics of the formation. These additional formation characteristics may then be used as part of additional algorithms used to control downhole operations such as stimulation, geosteering, and general drilling. Controlling downhole operations may include aiding in the determination to perform downhole operations, or controlling how the downhole operations are performed and where they are directed.

As would be appreciated by one of ordinary skill in the art in view of this disclosure, some or all of the steps from FIG. 3, may be performed in an information handling systems similar to the information handling system described in FIG. 2, with a processor and a memory containing a set of instructions that cause the information handling system to perform certain functions. For example, the set of instructions, when executed by a processor, may cause the system to receive pyrolysis data from a wellbore disposed in a formation and receive a thermal characteristic of the formation proximate to the wellbore. As described above, both the pyrolysis data and thermal characteristic may be found in a data set stored in a data storage device coupled to the information handling system. The processor may then calculate a kerogen porosity of the formation based, at least in part, on the pyrolysis data and the thermal characteristic. The calculations may utilize the same or similar equations as those described above with respect to FIG. 3. In certain embodiments, the system may also output commands to control a downhole operation based on the calculated kerogen porosity.

In addition to the method described with respect to FIG. 3, an additional method according to aspects of the present disclosure may include obtaining pyrolysis data from a plurality of wellbores disposed in a formation. This may require that core samples are retrieved from the wellbores and processed, and that a combined data set is generated. The method may also include determining a time-temperature burial history of the formation, such as the history illustrated in FIG. 4. A kerogen porosity at each of the plurality of wellbores may be calculated based, at least in part, on the corresponding pyrolysis data and the time-temperature burial history of the formation. Notably, by incorporating data points from multiple wellbores within a formation, the kerogen porosity of the entire formation may be characterized. For example, the method may also include at step 306 of FIG. 3 generating a kerogen porosity map of the formation based on the calculated kerogen porosity values. The kerogen porosity map may indicate where and how the kerogen porosity values change, allowing the determination of a new kerogen porosity value for a wellbore without available pyrolysis data, using the kerogen porosity map.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Also, the terms in the claims have their plain, ordinary meaning unless otherwise explicitly and clearly defined by the patentee. The indefinite articles "a" or "an," as used in the claims, are defined herein to mean one or more than one of the element that it introduces. The term "gas" is used within the scope of the claims for the sake of convenience in representing the various equations. It should be appreciated that the term "gas" in the claims is used interchangeably with the term "oil" as the kerogen porosity calculation applies equally to a formation containing kerogen that produces gas, and a formation containing kerogen that produces oil.

What is claimed is:

1. A method for determining kerogen porosity of a formation for downhole operations, comprising:

obtaining pyrolysis data from a wellbore disposed in a formation;

determining a thermal characteristic of the formation proximate to the wellbore, wherein the thermal characteristic comprises a time-temperature burial history of the formation;

calculating a kerogen porosity of the formation based, at least in part, on the pyrolysis data and the thermal characteristic, wherein calculating the kerogen porosity comprises solving equation (1):

$$\varphi_{pk} = TOC_i * C_c * k * TR * p_b / p_k \qquad (1)$$

where $\varphi_{pk}$ comprises a non-solid volume of a porous kerogen in the formation, $TOC_i$ comprises an initial organic carbon weight fraction of the formation, $C_c$ comprises a fraction of carbon in the formation that is convertible to hydrocarbon, k comprises a scale factor representing a kerogen mass equivalent to a convertible carbon mass, TR comprises a transformation ratio of the porous kerogen, $p_b$ comprises a formation density and $p_k$ comprises a kerogen density, and wherein calculating TR comprises:

applying a kinetic model of kerogen cracking to the time-temperature burial history, wherein applying the kinetic model of kerogen cracking to the time-temperature burial history comprises inputting the time-temperature burial history into a system of concurrent first-order Arrhenius reaction; and correlating an output of the kinetic model with at least one vitrinite reflectance value; and performing a downhole operation based, at least in part, on the calculated kerogen porosity.

2. The method of claim 1, wherein solving equation (1) comprises calculating $TOC_i$ and $C_c$ for the formation using at least one of the pyrolysis data and the time-temperature burial history.

3. The method of claim 2, wherein calculating $TOC_i$ for the formation comprises solving equation (3):

$$TOC_i = TOC + ((S_2 * TR * \alpha)/(1-TR)) \qquad (3)$$

where $S_2$ comprises a remaining hydrocarbon potential of pyrolysis sample, and α comprises an average carbon weight fraction in hydrocarbons formed during conversion of kerogen.

4. The method of claim 1, wherein the at least one vitrinite reflectance value is based, at least in part, on the time-temperature burial history.

5. The method of claim 2, wherein calculating $C_c$ for the formation comprises solving equation (2):

$$C_c = 0.085*(S_{2i}/TOC_i) \quad (2)$$

where $S_{2i}$ comprises an original hydrocarbon generation potential of the formation.

6. A system for determining kerogen porosity of a formation for downhole operations, comprising:
 a processor; and
 a tangible non-transitory memory device coupled to the processor, wherein the memory device comprises a set of instructions that, when executed by the processor, cause the system to:
  receive pyrolysis data from a wellbore disposed in a formation;
  receive a thermal characteristic of the formation proximate to the wellbore, wherein the thermal characteristic comprises a time-temperature burial history of the formation; and
  calculate a kerogen porosity of the formation based, at least in part, on the pyrolysis data and the thermal characteristic, wherein the set of instructions when executed by the processor further cause the system to calculate the kerogen porosity by solving equation (1):

$$\varphi_{pk} = TOC_i * C_c * k * TR * p_b/p_k \quad (1)$$

where $\varphi_{pk}$ comprises a non-solid volume of a porous kerogen in the formation, $TOC_i$ comprises an initial organic carbon weight fraction of the formation, $C_c$ comprises a fraction of carbon in the formation that is convertible to hydrocarbon, k comprises a scale factor representing a kerogen mass equivalent to a convertible carbon mass, TR comprises a transformation ratio of the porous kerogen, $p_b$ comprises a formation density and $p_k$ comprises a kerogen density, and wherein calculating TR comprises:
 applying a kinetic model of kerogen cracking to the time-temperature burial history, wherein applying the kinetic model of kerogen cracking to the time-temperature burial history comprises inputting the time-temperature burial history into a system of concurrent first-order Arrhenius reaction; and
 correlating an output of the kinetic model with at least one vitrinite reflectance value.

7. The system of claim 6, wherein solving equation (1) comprises calculating $TOC_i$ and $C_c$ for the formation using at least one of the pyrolysis data and the time-temperature burial history.

8. The system of claim 7, wherein calculating $C_c$ for the formation comprises solving equation (2):

$$C_c = 0.085*(S_{2i}/TOC_i) \quad (2)$$

where $S_{2i}$ comprises an original hydrocarbon generation potential of the formation.

9. The system of claim 7, wherein calculating $TOC_i$ for the formation comprises solving equation (3):

$$TOC_i = TOC + ((S_2 * TR * α)/(1-TR)) \quad (3)$$

where $S_2$ comprises a remaining hydrocarbon potential of pyrolysis sample, and α comprises an average carbon weight fraction in hydrocarbons formed during conversion of kerogen.

10. The system of claim 6, wherein the at least one vitrinite reflectance value is based, at least in part, on the time-temperature burial history.

11. A method for determining kerogen porosity of a formation for downhole operations, comprising:
 obtaining pyrolysis data from a plurality of wellbores disposed in a formation;
 determining a time-temperature burial history of the formation;
 calculating a kerogen porosity at each of the plurality of wellbores based, at least in part, on the corresponding pyrolysis data and the time-temperature burial history of the formation, wherein calculating the kerogen porosity comprises solving equation (1):

$$\varphi_{pk} = TOC_i * C_c * k * TR * p_b/p_k \quad (1)$$

where $\varphi_{pk}$ comprises a non-solid volume of a porous kerogen in the formation, $TOC_i$ comprises an initial organic carbon weight fraction of the formation, $C_c$ comprises a fraction of carbon in the formation that is convertible to hydrocarbon, k comprises a scale factor representing a kerogen mass equivalent to a convertible carbon mass, TR comprises a transformation ratio of the porous kerogen, $p_b$ comprises a formation density and $p_k$ comprises a kerogen density, and wherein calculating TR comprises:
 applying a kinetic model of kerogen cracking to the time-temperature burial history, wherein applying the kinetic model of kerogen cracking to the time-temperature burial history comprises inputting the time-temperature burial history into a system of concurrent first-order Arrhenius reaction; and
 correlating an output of the kinetic model with at least one vitrinite reflectance value, wherein the correlating comprises fitting a correlation function between the transformation ratio and the at least one vitrinite reflectance; and
 performing a downhole operation based, at least in part, on the calculated kerogen Porosity.

12. The method of claim 11, wherein solving equation (1) comprises calculating $TOC_i$ and $C_c$ for the formation using at least one of the pyrolysis data and the time-temperature burial history.

13. The method of claim 12, wherein calculating $C_c$ for the formation comprises solving equation (2):

$$C_c = 0.085*(S_{2i}/TOC_i) \quad (2)$$

where $S_{2i}$ comprises an original hydrocarbon generation potential of the formation.

14. The method of claim 12, wherein calculating $TOC_i$ for the formation comprises solving equation (3):

$$TOC_i = TOC + ((S_2 * TR * α)/(1-TR)) \quad (3)$$

where $S_2$ comprises a remaining hydrocarbon potential of pyrolysis sample, and α comprises an average carbon weight fraction in hydrocarbons formed during conversion of kerogen.

15. The method of claim 11, wherein the at least one vitrinite reflectance value is based, at least in part, on the time-temperature burial history.

* * * * *